US008727535B2

(12) United States Patent
Hara

(10) Patent No.: US 8,727,535 B2
(45) Date of Patent: May 20, 2014

(54) PERIMETER AND METHOD OF CONTROLLING PERIMETER

(75) Inventor: Takuya Hara, Shizuoka-ken (JP)

(73) Assignee: Kowa Company, Ltd., Aichi (JP)

( * ) Notice: Subject to any disclaimer, the term of this patent is extended or adjusted under 35 U.S.C. 154(b) by 692 days.

(21) Appl. No.: 12/868,055

(22) Filed: Aug. 25, 2010

(65) Prior Publication Data

US 2011/0234979 A1    Sep. 29, 2011

(30) Foreign Application Priority Data

Mar. 29, 2010 (JP) .................................. 2010-074142

(51) Int. Cl.
*A61B 3/00* (2006.01)
*A61B 3/02* (2006.01)

(52) U.S. Cl.
USPC .......................................... 351/224; 351/200

(58) Field of Classification Search
USPC ......... 351/200, 205, 208, 211, 222, 224, 226, 351/246
See application file for complete search history.

(56) References Cited

U.S. PATENT DOCUMENTS 7,178,737 B2 *    2/2007 Ohyama ....................... 235/492
2008/0036966 A1 *    2/2008 Shimada ....................... 351/224

FOREIGN PATENT DOCUMENTS

JP    S62-009330 A1    2/1987
JP    H04-003213 A1    1/1992
JP    2002-272685 A1    9/2002

* cited by examiner

*Primary Examiner* — Thomas K Pham
*Assistant Examiner* — Brandi Thomas
(74) *Attorney, Agent, or Firm* — Duane Morris LLP

(57) ABSTRACT

A perimeter according to the invention has fixation state detecting means for detecting a fixation state of an examinee in association with each portion where a stimulus should be presented, and necessity of retest is judged for each stimulus. Even if no good fixation state is detected for some stimulus, it is sufficient to retest the portion where the stimulus was presented. Then, burdens on the examinee or an examiner are lighter and the test time is shorter, and test efficiency is increased thereby.

3 Claims, 4 Drawing Sheets (a)

(b)

(c)

PERIMETER AND METHOD OF CONTROLLING PERIMETER

CROSS REFERENCE TO RELATED APPLICATION

The present disclosure relates to subject matter contained in Japanese patent application No. 2010-74142 filed on Mar. 29, 2010, the disclosure of which is expressly incorporated herein by reference in its entirety.

BACKGROUND OF THE INVENTION

This invention relates to a perimeter for measuring a visual field of an examinee in such a state that the examinee fixates a fixation target.

BACKGROUND ART

When suffering from an ophthalmic disease, such as glaucoma and diabetic retinopathy, it is known that a person has a visual field contraction or a visual field defect. For these reasons, perimeters having various structures have been proposed as devices for finding such diseases (see Japanese patent application the publication number of which is 2002-272685).

In order to correctly conduct perimetry with such a perimeter, it is important for an examinee to continuously fixate a fixation target. But, the examinee, especially an elder and a person who suffers from an ophthalmic disease, is difficult to bear a big burden of continuous fixation on the same fixation target from start to finish of the perimetry, and may look away from the fixation target.

Under such a situation, various kinds of devices for measuring the fixation state of the examinee have been proposed (see Japanese patent application publication Nos. S62-9330 and H04-3213), and a graph showing the fixation states is displayed with results of the perimetry. FIG. 4 is a view that shows a graph of change of a pupil position displayed in a test result table of a Humphrey perimeter. A longitudinal axis shows amount of deviation of pupil from a fixation target (rotational angle of eye ball: deg) and a traverse axis shows time from start of perimetry. An examiner judges whether the fixation state at the time of perimetry is good or not, watching such a graph, and the whole perimetry is conducted again if no good fixation state is judged. In other words, the perimetry is conducted again for the whole time zones of $H_1$ and $H_2$ even if retest is judged to be necessary due to no good fixation state in time zone $H_2$ only.

However, the above-mentioned conventional testing method has such a problem that perimetry data at the time when the fixation state was good (the perimetry data in time zone $H_1$) becomes vain since the whole perimetry (that is, $H_1$ and $H_2$ in FIG. 4) is conducted again although no good fixation state is only apart (see $H_2$ in FIG. 4). Besides, time for retest becomes longer and burdens on the examinee and the examiner become heavier thereby.

The object of the invention is to provide a perimeter for solving the above-mentioned problems and a method of controlling the perimeter.

SUMMARY OF THE INVENTION

One aspect of the invention is a perimeter for measuring a visual field of an examinee in such a state the examinee fixates a predetermined fixation target, comprising:

stimulus presentation means for presenting a stimulus having predetermined luminance in order at a plurality of portions where stimulus should be presented;

operation means to be operated by the examinee who perceived the presented stimulus;

visual field judging means for judging the visual field of the examinee based upon signals from the stimulus presentation means and the operation means;

fixation state detecting means for detecting fixation state of the examinee in order in association with each portion where the stimulus should be presented;

standard value setting means for setting a standard value which is a basis as to whether retest of the visual field is necessary or not in the fixation state; and retest judging means for judging as to whether retest is necessary or not for each portion where the stimulus should be presented by comparing each fixation state detected by the fixation state detecting means in order and the standard value set by the standard value setting means.

Another aspect of the invention is the perimeter, wherein the retest judging means judges the portion where the stimulus was presented but the fixation state was not detected by the fixation state detecting means to "be necessary to be retested".

Another aspect of the invention is the perimeter, further comprising retest execution means for conducting a retest of the visual field in such a way that the stimulus presentation means is controlled to present the stimulus again to the portion where the stimulus should be presented that was judged to be necessary to be retested through the retest judging means, and the visual field judging means judges the visual field of the examinee based upon signals from the stimulus presentation means and the operation means.

Another aspect of the invention is the perimeter, further comprising means for outputting discriminant figure of the fixation state showing the fixation state detected by the fixation state detecting means in order in association with the portion where the stimulus should be presented.

Another aspect of the invention is the perimeter according to claim 1, wherein the standard value setting means can manually change the standard value.

Another aspect of the invention is the perimeter, wherein if the fixation state exceeding the standard value is almost continuously detected predetermined times or more, the retest judging means judges "a point of time when the fixation state started to exceed the standard value" as a retest start point of time" and if the fixation state being lower than the standard value is almost continuously detected predetermined times or more thereafter, the retest judging means judges "a point of time when the fixation state started to become lower than the standard value" as a point of time of finish of retest.

Another aspect of the invention is the perimeter, further comprising means for outputting discriminant figure that shows the fixation state detected by the fixation state detecting means in order in association with each portion where the stimulus should be presented, and the means for outputting discriminant figure outputs the discriminant figure of the fixation state so as to discriminate the portions judged to be necessary to be retested and not necessary to be retested from each other through said retest judging means.

Another aspect of the invention is a perimeter for measuring a visual field of an examinee in such a state the examinee fixates a predetermined fixation target, comprising:

stimulus presentation means for presenting a stimulus having predetermined luminance at a plurality of portions where stimulus should be presented;

operation means to be operated by the examinee who perceived the presented stimulus;

visual field judging means for judging the visual field of the examinee based upon signals from the stimulus presentation means and the operation means;

fixation state detecting means for detecting the fixation state of the examinee in order in association with each portion where stimulus should be presented;

means for outputting a discriminant figure of the fixation state that shows the time series fixation states detected by the fixation state detecting means; and retest designating means for designating a time zone where retest is conducted in the discriminant figure of the fixation state.

Another aspect of the invention is a method of controlling a perimeter, comprising:

a step of presenting a stimulus having predetermined luminance at a plurality of portions where stimulus should be presented in order through stimulus presentation means;

a step of judging a visual field of an examinee by visual field judging means based upon signals outputted through operation of operation means by the examinee who perceived the presented stimulus and signals from stimulus presentation means;

a step of detecting a fixation state of the examinee in connection with each portion where the stimulus should be presented in order through fixation state detecting means;

a step of setting a standard value that is a basis whether a retest of the visual field is necessary or not by standard value setting means; and a step of judging as to whether a retest is necessary or not to each portion where the stimulus should be presented through retest judging means by comparing each fixation state detected in order through the fixation state detecting means and the standard value that is set through the standard value setting means.

Another aspect of the invention is the method of controlling the perimeter, further comprising:

a step of present the stimulus again to the portion that was judged to be necessary to retest by the retest judging means by controlling the stimulus presentation means through retest execution means; and a step of conducting a retest of the visual field by judging the visual field of the examinee by the visual field judging means based upon the signals from the stimulus presentation means and the operation means.

Another aspect of the invention is the method of controlling the perimeter, further comprising:

a step of outputting the discriminant figure of the fixation state that shows the fixation state detected in order by the fixation state detecting means in association with the portion where the stimulus should be presented through the means for outputting discriminant figure; and the means for outputting discriminant figure outputs the discriminant figure of the fixation state so as to discriminate the portions judged to be necessary to retest and to be not necessary to retest by the retest judging means from each other.

According to these aspects of the invention, judgments as to whether retest is necessary or not are respectively made in association with the respective locations where the stimulus is presented. In other words, measurement points having high credibility and lower credibility can be discriminated from each other. It is sufficient to retest only the location where the stimulus is presented that is judged to be necessary to be retested. Therefore, burdens on the examiner and examinee are lighter and time for retest is shorter, and the test efficiency becomes good in comparison with a case where the whole perimetry is retried from the first as a conventional way. And, the perimetry data at the time of good fixation state is of some use without discarding.

DESCRIPTION OF THE PREFERRED EMBODIMENTS

Figure 1:
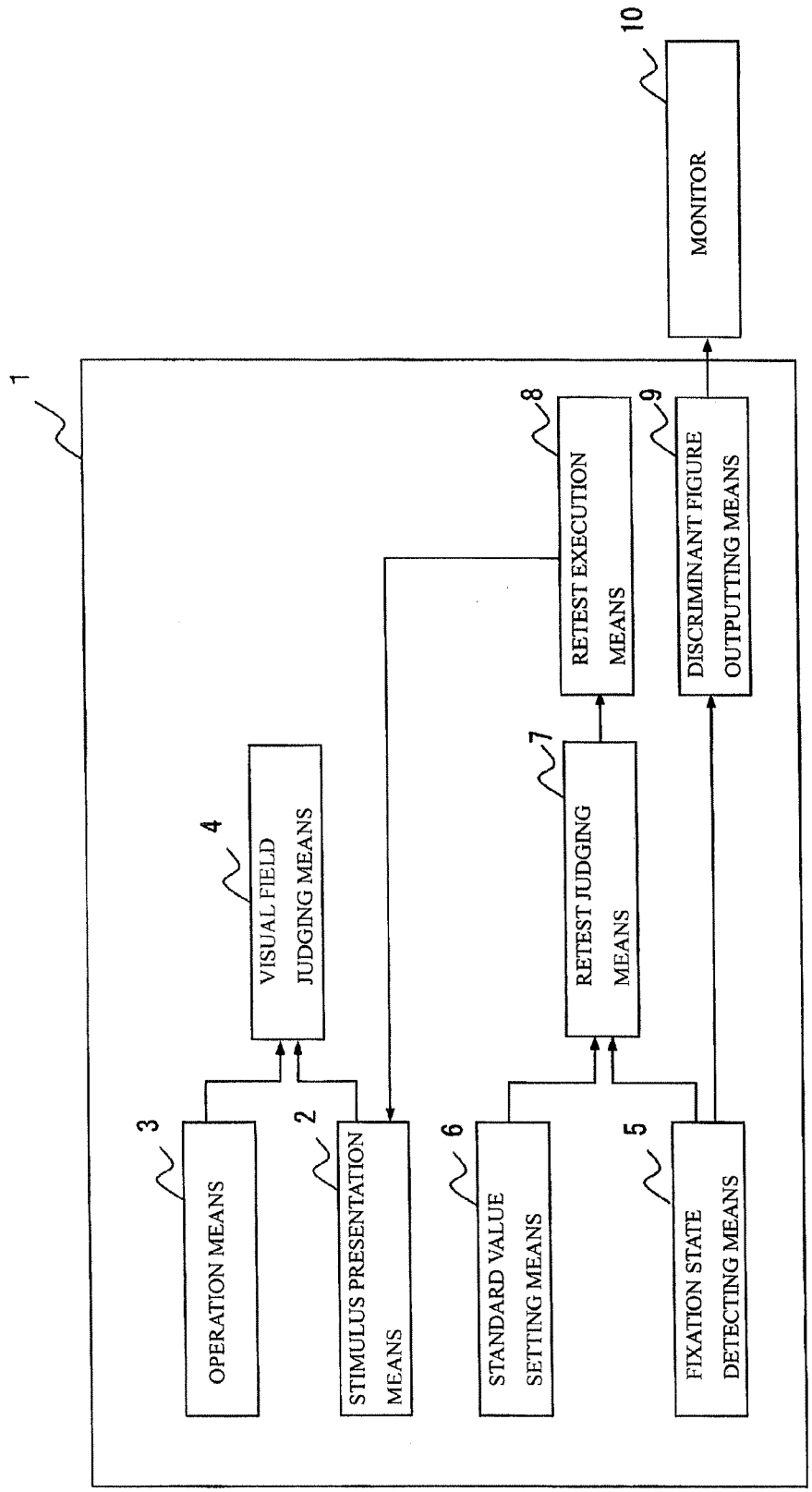
FIG. 1 is a block diagram showing an instance of a structure of a perimeter according to the invention.
Figure 2:
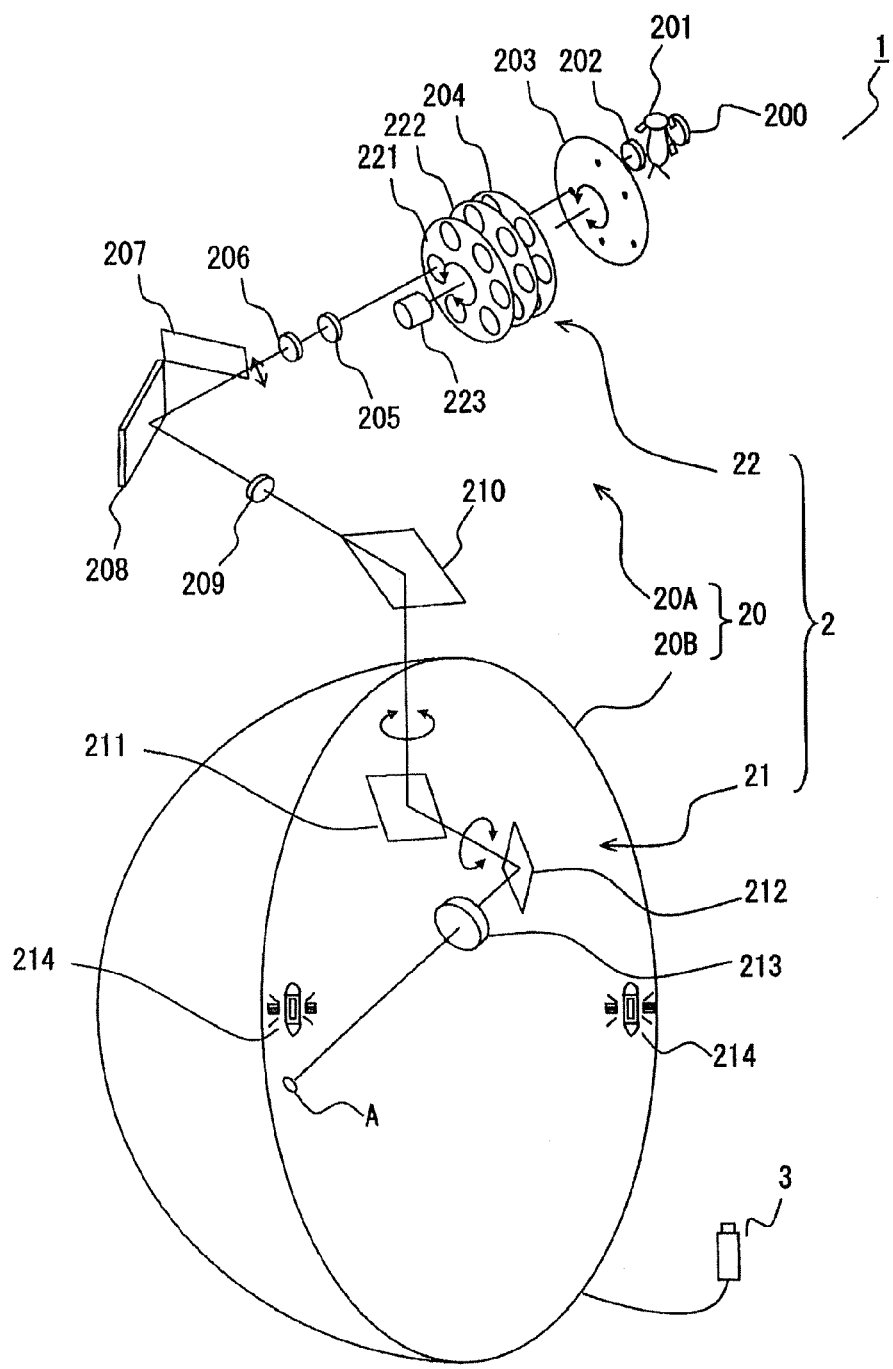
FIG. 2 is a typical view showing an instance of a structure of the perimeter (especially, stimulus presentation means) according to the invention.
Figure 3:
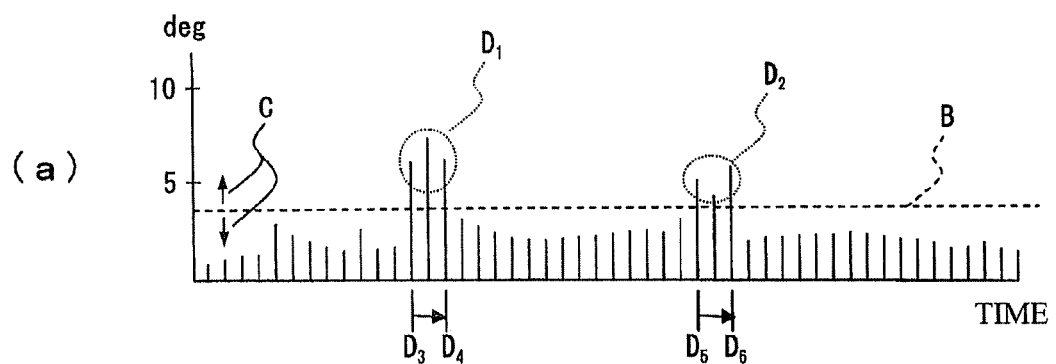
FIG. 3(a) to (c) are views of discriminant figures of fixation states.
Figure 3:
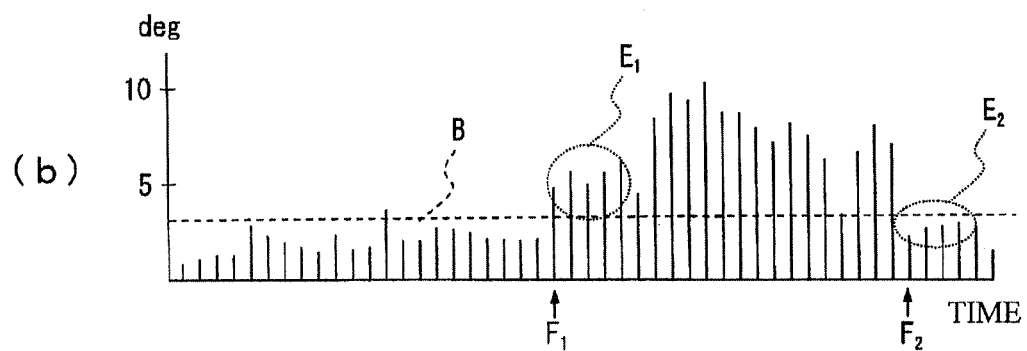
Figure 3:
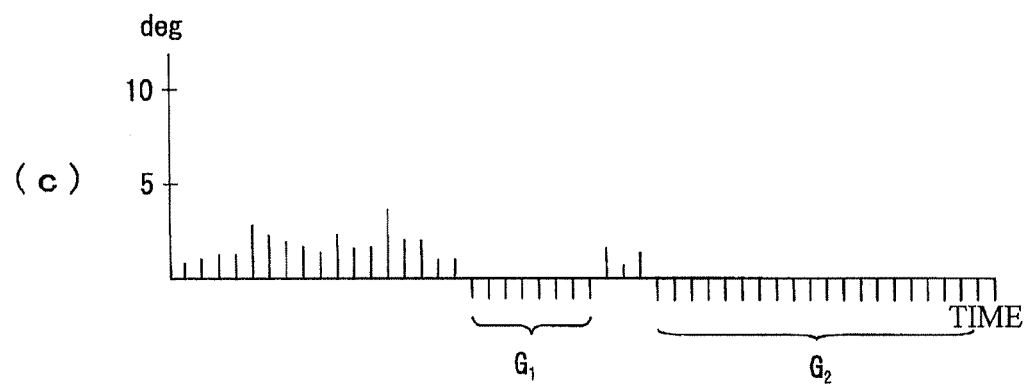
Figure 4:
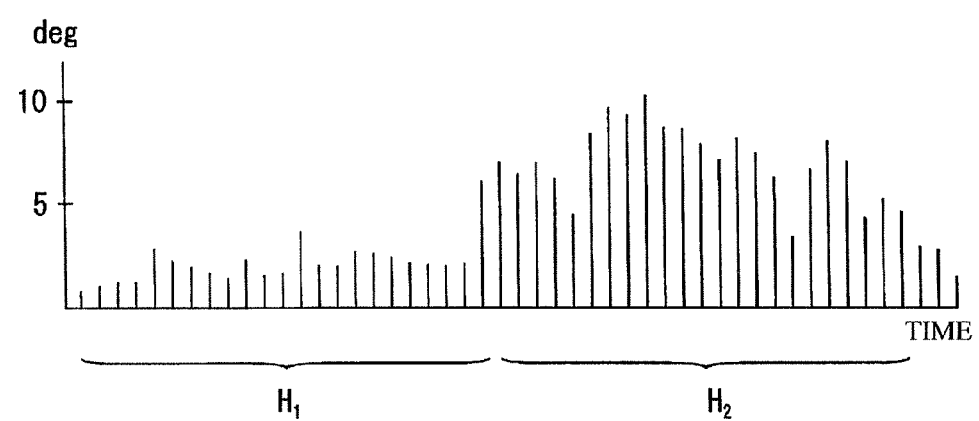
FIG. 4 is a view of an instance of a graph showing change of pupil position shown in a test result table of a Humphrey perimeter.

An embodiment of the invention is mentioned, referring to appended figures FIGS. 1 to 3.

A perimeter according to the invention is constructed so as to measure a visual field of an examinee (perimetry) in such a state that the examinee fixates a predetermined fixation target, such as a center point of a visual field dome B shown in FIG. 2). Such a perimeter is exemplarily shown with a reference number, 1 in FIG. 1 or FIG. 2, and has stimulus presentation means 2 (will be mentioned in detail) for presenting a stimulus A having predetermined luminance at a plurality of peripheral portions of the fixation target in order.

Such an perimeter 1 is provided with operation means 3, such as a push switch. An examinee can operate the operation means 3 when perceiving the presented stimulus A, through which signals showing the perception of the stimulus are transmitted.

The perimeter 1 according to the invention has visual field judging means 4 for judging the visual field of the examinee based upon the signals from the stimulus presentation means 2 and the operation means 3 so as to judge whether or not the examinee can perceive the stimulus at the respective stimulus presentation portions. Preferably, such visual field judging means 4 makes judgments according to kinds of perimetry, such as a screening perimetry, a threshold perimetry and an isopter perimetry.

In addition, the perimetry 1 according to the invention has fixation state detecting means 5 for detecting a fixation state of an examinee in order in association of each portion where the stimulus should be presented, standard value setting means 6 for setting a standard value that is a basis as to whether the fixation state needs to retest the visual field, and retest judging means 7 for judging as to whether retest is necessary or not for each portion where the stimulus should be presented by comparing each fixation state detected in order by the fixation state detecting means 5 and the standard value set by the standard value setting means 6 with each other.

According to the invention, necessity of retest is individually judged in association with each portion where the stimulus should be presented. In other words, a measurement point having high credibility and a measurement point having low credibility can be discriminated from each other. Then, it is sufficient to retest only the portion where the stimulus was presented that was judged to be necessary to be retested, and burdens on the examinee and examiner are lighter in comparison with a case where the whole test is done from the first.

In addition, test time is made shorter and efficiency of the test is made better. Besides, perimetry data at the time of good fixation state is not useless as a conventional way.

If the perimeter according to the invention is used, it is possible to continue to retest till the portion where fixation state is not good disappears. But, only the tests for twice times, first perimetry and retest thereafter, are mentioned in the specification for easy understanding. The first perimetry is referred to as "the first test" and the next perimetry to be conducted for the portion where the fixation state is not good is referred to as "the retest" for each understanding, and both perimetries are referred to as only "tests" if discrimination of both is not necessary.

The fixation state detecting means 5 is not possible to detect the fixation state if the examinee closed his eyes in the first test (see $G_1$ and $G_2$ of FIG. 3(c)). Preferably, the retest judging means 7 judges the portion where the stimulus was presented but the fixation state was not detected to be "necessary to be retested".

Retest execution means 8 may be provided for executing retest of the visual field for the portion where the retest is judged to be necessary by the retest judging means 7. Concretely speaking, the retest execution means 8 executes the retest in such a way that the stimulus presentation means 2 is controlled to represent the stimulus again to the portion where the retest was judged to be necessary by the retest judging means 7, and the visual field of the examinee is judged by the visual field judging means 4 based upon signals from the stimulus presentation means 2 and the operation means 3.

Accuracy of the necessary test (accuracy of perimetry) depends on objects (kinds) of the test. Preferably, the examiner can select the standard value according to the objects or kinds of the test by manually changing the standard value (not setting a constant standard value) through the standard value setting means 6. In such a case, the standard value setting means 6 may be a switch, such as volume control, a user interface displayed on a monitor screen and the other well-known means.

It is preferable to provide discriminant figure outputting means 9 for outputting a figure showing results detected by the above-mentioned fixation state detecting means 5 (that is the figure through which the fixation state in the portion where each stimulus is presented is known and is the figure showing the fixation state detected by the fixation state detecting means 5 in order in association with each portion where the stimulus is presented) to a monitor 10 or a printer (not shown). FIG. 3(a) is the view showing an example of such a discriminant figure of the fixation state (bar graph) wherein a longitudinal axis shows deviation of a pupil from a fixation target (rotational angle of an eye ball: deg) and a transverse axis shows time from start of perimetry (that is, start of first test). That is, the time-series fixation states detected by the fixation state detecting means 5 in order are shown in the figure. If time when no good fixation occurred (time from the start of the first test) is known, the portion where the stimulus was presented at such a time is specified. A broken line B in the figure shows a standard value in connection with the deviation (the standard value to be adjusted by the standard value setting means 6). Since a general size of a blind spot is 5° or so in its diameter, the standard value may be about 2.5° that is a half (radius) thereof.

The standard value setting means 6 may manually set the standard value before the first test, but may be set before the retest after the first test, watching the discriminant figure of the fixation state. In other words, preferably, the examiner manually operates the standard value setting means 6 so as to adjust the standard value B, watching the discriminant figure of the fixation state (see arrow C), the retest execution means 8 controls the stimulus presentation means 2 to present the stimulus again at a predetermined portion (that is, the portion where the retest was judged to be necessary by the retest judging means 7), and the visual field of the examinee is judged by the visual field judging means 4 based upon the signals from the stimulus presentation means 2 and the operation means 3. In case of the detected result of FIG. 3(a), the deviation exceeds the standard value B at the portions as shown by reference numerals $D_1$ and $D_2$. So, the retest execution means 8 presents the stimulus again at the portions where the stimulus was presented at the times $D_1$ and $D_2$ so as to execute the retest.

In FIG. 3(a), the standard value that is manually adjusted by the standard value setting means 6 relates to the deviation of the longitudinal axis (the rotational angle of the eye ball), but the standard value may be set in connection with time of the transverse axis. In other words, the above-mentioned retest may be conducted in such a manner that the examiner operates some operation means (retest designating means for designating time zone in which retest should be conducted in the discriminant figure of the fixation state), watching this graph so as to designate a point of time when retest is started (the standard value in connection with time, such as $D_3$ and $D_5$), and a point of time when retest is finished (the standard value in connection with time, such as $D_4$ and $D_6$), and the retest execution means 8 controls the stimulus presentation means 2 so as to execute the retest by presenting the stimulus again at the portions where the stimulus was presented at such time zones ($D_3$ to $D_4$ and $D_5$ to $D_6$). Alternatively, selection means for selecting as to whether the standard value of the longitudinal axis or the standard value of the transverse axis is adjusted, a switch or a user interface displayed on a monitor screen, may be provided and the examiner may select one of both.

If the fixation state exceeding the standard value is almost continuously detected predetermined times or more (see reference mark $E_1$ of FIG. 3(b), for example), the retest judging means 7 may judge "the point of time when the fixation state starts to exceed the standard value, such as the point of time as shown with a reference mark $F_1$" as "retest start time". If the fixation state being lower than the standard value is almost continuously detected predetermined times or more thereafter (see reference mark $F_2$ of FIG. 3(b), for example), the retest judging means 7 may judge "the point of time when the fixation state starts to become lower the standard value, such as the point of time as shown by a reference mark $F_2$ in FIG. 3(b)" as retest finish time. In a case of the method as shown in FIG. 3(b), the time for retest can be shortened although in case of the method as shown in FIG. 3(a), retest is executed for all portions where the deviation exceeds the standard value B and it takes a longer time for retest thereby.

In the discriminant figure of the fixation state as shown in FIGS. 3(a) to (c), a longitudinal axis denotes the rotational angle of the eye ball and a transverse axis denotes time, but the other type of the discriminant figure of the fixation state may be outputted. For example, the longitudinal axis may denote some value showing the fixation state and the transverse axis may denote some value through which the portion where the stimulus is presented is known. In addition, the figure may be a graph excluding a bar graph or a table. In other words, any discriminant figure of the fixation state is available as long as the figure is a graph or a table that shows the fixation state at the time when each stimulus is presented in association with the portion where the stimulus is presented, such as the fixation state at the time when the first stimulus is presented, the fixation state at the time when the second stimulus is presented, . . . .

On the other hand, the above-mentioned discriminant figure outputting means 9 may be provided and the discriminant figure outputting means 9 outputs the discriminant figure of the fixation state so as to discriminate the portions that are judged to be necessary to be retested and not necessary to be retested by the retest judging means from each other. As one of the methods of discriminating is to highlight the portion where the fixation state is not good.

Preferably, the above-mentioned fixation state detecting means 5 is comprised of a photographing portion, such as an infrared CCD, for obtaining successive images by photographing a front eye of an examinee. The fixation state detecting means 5 may have an image processing portion for processing images obtained by the photographing portion in order to extract a pupil of an examinee and obtaining a center of the pupil, in addition to the photographing portion. In addition, the fixation state detecting means 5 may have deviation amount computing portion for computing amount of deviation of the center of pupil to the standard position (the position of the center of the pupil when the examinee correctly fixates the fixation target) in addition to the photographing portion and the image processing portion.

On the other hand, a method of controlling the perimeter according to the invention according to the invention has a step of presenting the stimulus having predetermined luminance at a plurality of portions in order through the stimulus presentation means 2;

a step of judging the visual field of the examinee through the visual field judging means 4 based upon signals outputted by the examinee who perceived the presented stimulus through the operation means 3 and signals from the stimulus presentation means 2;

a step of detecting the fixation state of the examinee in connection with each portion where the stimulus is presented in order through the fixation state detecting means 5;

a step of setting the standard value that is a basis whether the retest of the visual field is necessary or not in the fixation state through the standard value setting means 6; and a step of judging as to whether the retest is necessary or not for each portion where the stimulus is presented through the retest judging means 7 by comparing each fixation state detected in order through the fixation state detecting means 5 and the standard value that is set through the standard value setting means 6.

Such a method may has a step of representing the stimulus again to the portion that was judged to be necessary to retest by the retest judging means 7 by controlling the stimulus presentation means 2 through the retest execution means 8; and a step of conducting a retest of the visual field by judging the visual field of the examinee by the visual field judging means 4 based upon the signals from the stimulus presentation means 2 and the operation means 3.

Besides, the method may has a step of outputting the discriminant figure of the fixation state that shows the fixation states detected in order by the fixation state detecting means 5 in association with the portions where the stimulus is presented through the discriminant figure outputting means 9. And, the discriminant figure outputting means 9 may output the discriminant figure of the fixation state so as to discriminate the portions judged to be necessary to retest and not necessary to retest through the retest judging means 7 from each other.

A structure of the stimulus presentation means 2 as shown in FIG. 2 is mentioned briefly.

A reference number 20 in the figure denotes the stimulus presentation portion for presenting stimulus A in the visual field of the examinee, a reference numeral 21 denotes the presentation portion changing portion for changing the portion where the stimulus A is presented and a reference numeral 22 denotes the luminance setting portion for setting the luminance of the stimulus A.

The stimulus presentation portion 20 in the figure is comprised of a projection optical system 20A for projecting stimuli and projection member 20B where stimuli are projected by the projection optical system 20A, but may have any structure as long as the stimulus presentation portion 20 can present the stimuli in the visual field of the examinee. For example, a plurality of LEDs may be located and be selectively lighted. The projection member 20B has a semi-spherical dome shape (visual field dome), but may have a shape with a curved face excluding a semi-sphere or a shape with a plane.

If the stimulus presentation portion 20 is comprised of the projection optical system 20A and the projection member 20B as shown in FIG. 2, the presentation portion changing portion 21 may be comprised of driving means for changing positions of structural elements of the projection optical system 20A, such as projector mirrors 211, 212 (not shown). If the stimulus presentation portion is comprised of a plurality of LEDs, which LED should be lighted may be controlled by the presentation portion changing portion. Even if any of the projection optical system and LED is used, an examiner may manually instruct to change the portion to be presented with a touch pen, a mouse or a keyboard, watching a display, or the change of the portion to be presented may be automatically instructed through a program prepared in advance.

The luminance setting portion 22 as shown in FIG. 2 is comprised of turrets 221, 222 having a plurality of filters rotatably supported which attenuation is different and driving mechanism 223 for changing positions of the turrets 221, 222, but may have another structure.

The present invention has been explained on the basis of the example embodiments discussed. Although some variations have been mentioned, the embodiments which are described in the specification are illustrative and not limiting. The scope of the invention is designated by the accompanying claims and is not restricted by the descriptions of the specific embodiments. Accordingly, all the transformations and changes within the scope of the claims are to be construed as included in the scope of the present invention.

The invention claimed is:

1. A perimeter for measuring a visual field of an examinee in such a state the examinee fixates a predetermined fixation target, the perimeter comprising:

stimulus presentation means for presenting a stimulus having predetermined luminance in order at a plurality of portions where stimulus should be presented;

operation means to be operated by the examinee who perceived the presented stimulus;

visual field judging means for judging the visual field of the examinee based upon signals from the stimulus presentation means and the operation means;

fixation state detecting means for detecting fixation state of the examinee in order in association with each portion where the stimulus should be presented;

standard value setting means for setting a standard value which is a basis as to whether retest of the visual field is necessary or not in the fixation state;

retest judging means for judging as to whether retest is necessary or not for each portion where the stimulus should be presented by comparing each fixation state detected by the fixation state detecting means in order and the standard value set by the standard value setting means; and retest execution means for conducting a retest of the visual field in such a way that the stimulus presentation means is controlled to present the stimulus again to the portion where the stimulus should be presented that was judged to be necessary to be retested through the retest judging means, and the visual field judging means judges the visual field of the examinee based upon signals from the stimulus presentation means and the operation means.

2. A perimeter for measuring a visual field of an examinee in such a state the examinee fixates a predetermined fixation target, the perimeter comprising:

stimulus presentation means for presenting a stimulus having predetermined luminance in order at a plurality of portions where stimulus should be presented;

operation means to be operated by the examinee who perceived the presented stimulus;

visual field judging means for judging the visual field of the examinee based upon signals from the stimulus presentation means and the operation means;

fixation state detecting means for detecting fixation state of the examinee in order in association with each portion where the stimulus should be presented;

standard value setting means for setting a standard value which is a basis as to whether retest of the visual field is necessary or not in the fixation state; and retest judging means for judging as to whether retest is necessary or not for each portion where the stimulus should be presented by comparing each fixation state detected by the fixation state detecting means in order and the standard value set by the standard value setting means, wherein if the fixation state exceeding the standard value is almost continuously detected predetermined times or more, the retest judging means judges a point of time when the fixation state started to exceed the standard value as a retest start point of time and if the fixation state being lower than the standard value is almost continuously detected predetermined times or more thereafter, the retest judging means judges a point of time when the fixation state started to become lower than the standard value as a point of time of finish of retest.

3. A perimeter for measuring a visual field of an examinee in such a state the examinee fixates a predetermined fixation target, the perimeter comprising:

stimulus presentation means for presenting a stimulus having predetermined luminance in order at a plurality of portions where stimulus should be presented;

operation means to be operated by the examinee who perceived the presented stimulus;

visual field judging means for judging the visual field of the examinee based upon signals from the stimulus presentation means and the operation means;

fixation state detecting means for detecting fixation state of the examinee in order in association with each portion where the stimulus should be presented;

standard value setting means for setting a standard value which is a basis as to whether retest of the visual field is necessary or not in the fixation state; and retest judging means for judging as to whether retest is necessary or not for each portion where the stimulus should be presented by comparing each fixation state detected by the fixation state detecting means in order and the standard value set by the standard value setting means; and means for outputting discriminant figure that shows the fixation state detected by the fixation state detecting means in order in association with each portion where the stimulus should be presented, and the means for outputting discriminant figure outputs the discriminant figure of the fixation state so as to discriminate the portions judged to be necessary to be retested and not necessary to be retested from each other through said retest judging means, wherein the standard value setting means can manually change the standard value, the standard value setting means manually sets the standard value after the first test, watching the discriminant figure of the fixation state.

* * * * *